United States Patent
Van Der Heide et al.

(10) Patent No.: US 7,563,919 B2
(45) Date of Patent: *Jul. 21, 2009

(54) PROCESS FOR THE PREPARATION OF AN ALKANEDIOL AND A DIALKYL CARBONATE

(75) Inventors: Evert Van Der Heide, Amsterdam (NL); Timothy Michael Nisbet, Amsterdam (NL); Garo Garbis Vaporciyan, Houston, TX (US)

(73) Assignee: Shell Oil Company, Houston, TX (US)

( * ) Notice: Subject to any disclaimer, the term of this patent is extended or adjusted under 35 U.S.C. 154(b) by 111 days.

This patent is subject to a terminal disclaimer.

(21) Appl. No.: 11/677,999

(22) Filed: Feb. 22, 2007

(65) Prior Publication Data
US 2007/0197814 A1    Aug. 23, 2007

Related U.S. Application Data

(60) Provisional application No. 60/775,469, filed on Feb. 22, 2006.

(51) Int. Cl.
C07C 69/96    (2006.01)
C07C 27/00    (2006.01)

(52) U.S. Cl. ........................ 558/277; 568/867
(58) Field of Classification Search ........... None
See application file for complete search history.

(56) References Cited

U.S. PATENT DOCUMENTS

| | | | |
|---|---|---|---|
| 2,994,705 A | 8/1961 | Crosby et al. | 260/340.2 |
| 3,803,201 A | 4/1974 | Glipin et al. | 260/463 |
| 4,314,945 A | 2/1982 | McMullen et al. | 260/340.2 |
| 4,434,105 A | 2/1984 | Buysch et al. | 260/463 |
| 4,508,927 A | 4/1985 | Bhise et al. | 568/858 |
| 4,691,041 A | 9/1987 | Duranleeau et al. | 558/277 |
| 5,153,333 A | 10/1992 | Schubert et al. | 549/230 |
| 5,231,212 A | 7/1993 | Buysch et al. | 558/277 |
| 5,359,118 A * | 10/1994 | Wagner et al. | 558/277 |
| 5,426,207 A | 6/1995 | Harrison et al. | 558/274 |
| 5,449,791 A | 9/1995 | Wagner et al. | 549/230 |
| 5,455,368 A | 10/1995 | Janisch et al. | 58/277 |
| 5,508,442 A | 4/1996 | Wagner et al. | 549/228 |
| 5,847,189 A | 12/1998 | Tojo et al. | 558/277 |
| 6,156,160 A | 12/2000 | Marquis et al. | 203/29 |
| 6,187,972 B1 | 2/2001 | Kawabe et al. | 568/858 |
| 6,294,684 B1 | 9/2001 | de Bruin et al. | 558/274 |
| 6,380,419 B2 | 4/2002 | Kawabe | 558/277 |
| 6,392,078 B1 | 5/2002 | Ryu et al. | 558/277 |
| 6,407,279 B1 | 6/2002 | Buchanana et al. | 558/227 |
| 6,479,689 B1 | 11/2002 | Tojo et al. | 558/277 |
| 6,573,396 B2 | 6/2003 | Buchanan et al. | 558/277 |
| 6,774,256 B2 | 8/2004 | Schlosberg et al. | 558/277 |
| 2004/0059083 A1 | 3/2004 | Schlosberg et al. | 528/86 |

FOREIGN PATENT DOCUMENTS

| | | |
|---|---|---|
| CN | 1060091 | 4/1992 |
| CN | 1102826 | 5/1995 |
| CN | 1528735 | 9/2004 |
| EP | 0297647 | 6/1788 |
| EP | 0001082 | 3/1979 |
| EP | 0274953 | 7/1988 |
| EP | 0180387 | 5/1990 |
| EP | 0583789 | 2/1994 |
| EP | 0776890 | 1/2001 |
| EP | 1174406 | 1/2002 |
| EP | 0119840 | 9/2004 |
| JP | 55-64550 | 5/1980 |
| JP | 61-291545 | 12/1986 |
| JP | 2-212456 | 8/1990 |
| JP | 9-183744 | 7/1997 |
| JP | 2000-005503 | 1/2000 |
| JP | 2003-81893 | 3/2003 |
| JP | 2000-113144 | 4/2003 |
| JP | 2003-155264 | 5/2003 |
| JP | 2003-342236 | 12/2003 |
| WO | WO9957108 | 11/1999 |
| WO | WO03006418 | 1/2003 |
| WO | WO03082797 | 10/2003 |
| WO | WO2004056793 | 7/2004 |
| WO | WO2005003113 | 1/2005 |
| WO | WO2005051939 | 6/2005 |

* cited by examiner

Primary Examiner—Karl J Puttlitz

(57) ABSTRACT

An alkanediol and a dialkyl carbonate are prepared in a process comprising:
(a) contacting an alkylene carbonate with an alkanol feedstock under transesterification conditions in a reactive distillation zone to obtain a top stream comprising dialkyl carbonate and the alkanol and a bottom stream comprising an alkanediol;
(b) separating the top stream comprising dialkyl carbonate and the alkanol into an alkanol-rich stream and a dialkyl carbonate-rich stream;
(c) recovering the dialkyl carbonate from the dialkyl carbonate-rich stream; and
(d) recycling at least part of the alkanol-rich stream to the reactive distillation zone as part of the alkanol feedstock, wherein the alkanol-rich stream is split in at least two portions, and at least one portion is condensed and freed from compounds with a lower boiling point than the alkanol.

The process is especially suitable for the production of propylene glycol and dimethyl carbonate from propylene carbonate and methanol.

7 Claims, 2 Drawing Sheets

PROCESS FOR THE PREPARATION OF AN ALKANEDIOL AND A DIALKYL CARBONATE

This application claims the benefit of U.S. Provisional Application No. 60/775,469 filed Feb. 22, 2006.

FIELD OF THE INVENTION

The present invention relates to a process for the preparation of an alkanediol and a dialkyl carbonate. More particularly, the invention relates to a process for the preparation of such compounds from an alkylene carbonate and an alkanol.

BACKGROUND

Such a process is known from e.g. U.S. Pat. No. 5,359,118. This document discloses a process in which di($C_1$-$C_4$ alkyl) carbonates are prepared by transesterification of an alkylene carbonate with a $C_1$-$C_4$ alkanol. In this process the alkylene carbonate and an alkanol feedstock are reacted countercurrently in a column. The alkylene carbonate is introduced into the upper part of the column and trickles down from above. The alkanol feedstock comprising a pure alkanol and a stream, comprising the alkanol and also the dialkyl carbonate, is fed into the column at a lower part. The alkanol flows upward and reacts countercurrently with the alkylene carbonate to obtain dialkyl carbonate with unreacted alkanol as the top effluent and the alkanediol with any entrained alkanol as the bottom effluent. The top effluent is subjected to extractive distillation to yield an alkanol-rich stream comprising the alkanol and minor amounts of the dialkyl carbonate. This stream is fed to the column as part of the alkanol feedstock.

The process discloses the formation of high-boiling by-products, such as polyglycols. However, the known process does not address the problem of the build up of low-boiling by-products. Such by-products can for instance be carbon dioxide that may be formed due to the hydrolysis of alkylene carbonate by small amounts of water that may be present in the alkanol or any other starting material. Other by-products that may be formed include acetaldehyde, propionaldehyde, and acetone.

SUMMARY OF THE INVENTION

It has now been found that the build up of lower-boiling by-products can be prevented by creating a bleed stream in the alkanol. Accordingly, the present invention provides a process for the preparation of an alkanediol and a dialkyl carbonate comprising:

(a) contacting an alkylene carbonate with an alkanol feedstock under transesterification conditions in a reactive distillation zone to obtain a top stream comprising dialkyl carbonate and the alkanol and a bottom stream comprising the alkanediol;

(b) separating the top stream comprising dialkyl carbonate and the alkanol into an alkanol-rich stream and a dialkyl carbonate-rich stream;

(c) recovering the dialkyl carbonate from the dialkyl carbonate-rich stream; and (d) recycling at least part of the alkanol-rich stream to the reactive distillation zone as part of the alkanol feedstock, wherein the alkanol-rich stream is split in at least two portions, and at least one portion is condensed and freed from compounds with a lower boiling point than the alkanol.

DETAILED DESCRIPTION

Figure 1:
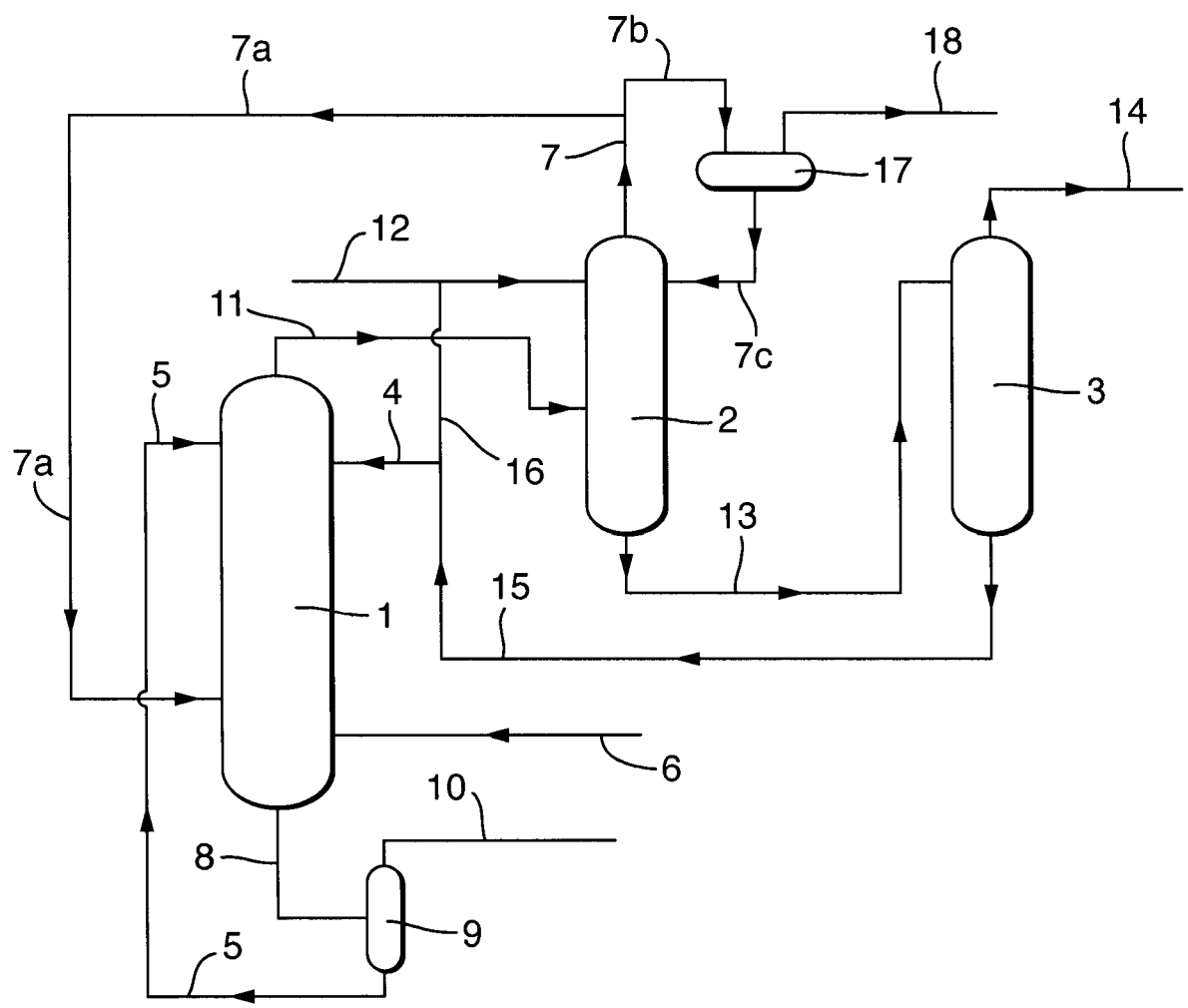
FIG. 1 is a schematic illustrating an embodiment of the invention in which the portion of the alkanol-rich stream that is freed from contaminants is recycled to the column for separation of alkanol and dialkylcarbonate in an extractive distillation zone.

According to the present invention the alkanol-rich stream from the top stream of the extractive distillation is split. At least one part is condensed. The condensation can be achieved in a number of ways. An advantageously used way is to pass the stream through a liquid or air cooler in order to condense at least part of the vapour. From the condensed liquid, vaporous lower boiling compounds are separated and removed from the process. In this way a building up of low-boiling compounds is prevented.

The process of the present invention includes the transesterification of an alkylene carbonate with an alkanol. This transesterification reaction is known, as is apparent from e.g. U.S. Pat. No. 5,359,118. The starting materials of the transesterification are preferably selected from $C_2$-$C_6$ alkylene carbonates and $C_1$-$C_4$ alkanols. More preferably the starting materials are ethylene carbonate or propylene carbonate and methanol, ethanol or isopropanol. The most preferred alkanols are methanol and ethanol.

The transesterification step is advantageously carried out in a column into which the alkylene carbonate is fed at the upper part, such that the alkylene carbonate flows down in counter current contact with upwardly moving alkanol. The product of the reaction is a dialkyl carbonate and an alkanediol. The dialkyl carbonate is recovered at the upper part of the column as the top stream. The alkanediol is recovered as the bottom stream.

The transesterification is suitably conducted in the presence of a catalyst. Suitable catalysts have been described in U.S. Pat. No. 5,359,118 and include hydrides, oxides, hydroxides, alcoholates, amides, or salts of alkali metals, i.e., lithium, sodium, potassium, rubidium and caesium. Preferred catalysts are hydroxides or alcoholates of potassium or sodium. It is advantageous to use the alcoholate of the alkanol that is being used as feedstock. Such alcoholate can be added as such or can be formed in situ.

Other suitable catalysts are alkali metal salts, such as acetates, propionates, butyrates, or carbonates. Further suitable catalysts are described in U.S. Pat. No. 5,359,118 and the references mentioned therein, such as EP-A 274 953, U.S. Pat. No. 3,803,201, EP-A 1082, and EP-A 180 387.

The transesterification conditions are known in the art and suitably include a temperature from 40 to 200° C., and a pressure from 50 to 400 kPa. Preferably, the pressure is close to atmospheric. The temperature depends on the alkanol feedstock and pressure used. The temperature is kept such that it is close to and above the boiling point of the alkanol, e.g. up to 5° C. above the boiling point. In the case of methanol and atmospheric pressure, the temperature is close to and above 65° C., for instance between 65 and 70° C.

The transesterification reaction is advantageously conducted in a column furnished with internals, like a distillation column. Hence, it may contain trays with bubble caps, sieve trays, or Raschig rings. The skilled person will realize that several packings and tray configurations will be possible. The alkylene carbonate will be fed at the upper part of such a column and will flow down. The alkylene carbonate will generally have a higher boiling point than the alkanol. In the case of ethylene and propylene carbonate the atmospheric boiling points are above 240° C. The alkylene carbonate will flow down over the trays or rings and will be brought into contact with the alkanol that flows upward. When the transesterification catalyst is homogeneous, such as an alkali metal alcoholate, it is also introduced in the upper part of the column. The alkanol feedstock is introduced at a lower point. The feedstock may be completely vaporous. However, it is also possible to introduce the feedstock into the column partly in the liquid phase. It is believed that the liquid phase ensures a higher concentration of alkanol in the lower part of the column with a beneficial effect on the overall transesterification. It is distributed over the width of the column via the inlet and the column internals. The ratio between the vaporous and the liquid part of the alkanol feedstock may be varied between wide ranges. The vapour/liquid weight ratio is suitably from 1:1 to 10:1 wt/wt.

The person skilled in the art will know that the transesterification is an equilibrium reaction. Therefore, he shall suitably employ an excess of the alkanol. The molar ratio of alkanol to alkylene carbonate is suitably from 5:1 to 25:1, preferably from 6:1 to 15:1, more preferably from 7:1 to 9:1. The amount of catalyst can evidently be much smaller. Suitable amounts include from 0.1 to 5.0% wt based on alkylene carbonate, preferably from 0.2 to 2% wt.

The reactive distillation results in a top stream containing the dialkyl carbonate and any excess unreacted alkanol, and a bottom stream containing the alkane diol and the catalyst. Due to some water that may be contained in the alkanol some hydrolysis of the alkylene carbonate may take place, forming alkanediol and carbon dioxide. Other low-boiling by-products or contaminants can be aldehydes, ketones and alkylene oxides.

The bottom stream is suitably subjected to a separation of the alkanediol. Thereto, the bottom stream is split suitably in a fractionation column into a catalyst-rich stream and a stream comprising the alkanediol and, optionally, some alkanol. After purification, e.g. by further distillation, the alkanediol is recovered as eventual product. The catalyst-rich stream is suitably recycled to the reactive distillation zone. Also any alkanol that is separated from the bottom stream can be recycled.

The top stream is subsequently separated into an alkanol-rich stream and a dialkyl carbonate-rich stream. This can suitably be done by distillation. However, as indicated in U.S. Pat. No. 5,359,118 many alkanols and their corresponding dialkyl carbonates form azeotropes. Therefore simple distillation may not be sufficient to achieve a satisfactory separation. Therefore it is preferred to use an extractant to facilitate the separation between the dialkyl carbonate and the alkanol. The extractant can be selected from many compounds, in particular alcohols such as phenol, or anisole. However, it is preferred to employ an alkylene carbonate as extractant. It is most advantageous to obtain the separation in the presence of the alkylene carbonate that is being used as starting material for the eventual alkanediol.

The extractive distillation is preferably conducted in two columns. In the first column separation is achieved between the alkanol and a dialkyl carbonate/alkylene carbonate mixture. In the second column the separation between the dialkyl carbonate and the alkylene carbonate is achieved. The alkylene carbonate is suitably recycled to the first column for renewed use as extractant. The ratios between alkylene carbonate and alkanol and alkylene carbonate and dialkyl carbonate can be varied between wide ranges. Suitable ranges include from 0.2 to 2 moles of alkylene carbonate per mole of the sum of alkanol and dialkyl carbonate, preferably from 0.4 to 1.0 moles per mole.

The distillation for these separation conditions can be selected within wide ranges, as the skilled person will realize. Pressures may suitably range from 5 to 400 kPa, and temperatures from 40 to 200° C. In view of the stability of alkylene carbonate the temperature is advantageously below 180° C., whereas the lower temperature is determined by the boiling point of the alkanol. When two distillation columns are used, it is preferred to conduct the separation between alkanol and dialkyl carbonate/alkylene carbonate mixture at a higher pressure, such as 60 to 120 kPa, and the second separation between dialkyl carbonate and alkylene carbonate at lower pressure, such as 5 to 50 kPa. This will allow a sufficiently low temperature to retain a satisfactory stability for the alkylene carbonate and an efficient separation between the carbonate compounds. The dialkyl carbonate obtained is recovered as product, optionally after further purification. This further purification may comprise a further distillation step or an ion-exchange step, as described in U.S. Pat. No. 5,455,368.

The alkanol-rich stream that is obtained is freed from low-boiling compounds. In one embodiment the top stream is split in two or more portions. At least one portion is cooled such that the alkanol condenses. Any low-boiling compound in the vaporous phase is removed. The condensed alkanol is then recycled to the reactive distillation zone. Although some low-boiling compounds may be entrained in the liquid phase the present process provides a satisfactory removal of such compounds. In another embodiment the liquid alkanol after condensation is recycled to step (b). When step (b) comprises a distillation the liquid portion of the alkanol is sent as reflux to the distillation. A combination of both recycles is also possible.

U.S. Pat. No. 5,359,118 mentions that the vaporous alkanol-rich stream from the distillation is recycled to the reactive distillation zone. It further describes that the recycle alkanol is introduced into the reactive distillation zone at a point above the introduction of pure make-up alkanol. According to the document the recycle stream contains other compounds, in particular the dialkyl carbonate.

In the present invention the alkanol-rich stream is split in at least two portions, two being usually sufficient. At least one portion is then compressed and recycled as vapour recycle stream to the reactive distillation zone. At least one other portion is condensed and freed from low-boiling compounds.

The weight ratio between the liquid and the vaporous split portions can be selected by the skilled person to arrive at the optimal effect. It is advantageous to split the alkanol-rich stream such that the weight ratio between the portion to be condensed and the vaporous portion is from 0.1:1 to 1:1. This will allow an efficient removal of contaminants.

As stated above, the alkanol-rich stream is suitably recycled to the reactive distillation zone. Therefore, the alkanol feedstock comprises advantageously make-up pure alkanol and the liquid and vaporous recycle streams. The recycle streams may be mixed with the make-up pure alkanol, and subsequently be introduced into the reactive distillation zone as the alkanol feedstock. It is also possible to combine either the liquid or the vaporous recycle stream with the make-up pure alkanol before introduction into the distillation zone. However, it is more preferred to introduce the make-up alkanol into the reactive distillation zone below the introduction of the liquid and the vaporous recycle streams. Thereby the advantages described in U.S. Pat. No. 5,359,118 are being obtained.

The process of the present invention can be employed for a variety of feedstocks. The process is excellently suited for the preparation of ethylene glycol, propylene glycol, dimethyl carbonate and/or diethyl carbonate. The process is most advantageously used for the production of propylene glycol (1,2-propane diol) and dimethyl carbonate from propylene carbonate and methanol.

In FIG. 1 a reactive distillation zone 1 and two extractive distillation zones 2 and 3 are shown. The process will now be explained by using propylene carbonate and methanol as examples. It is understood that a person skilled in the art can replace these examples with any other suitable alkylene carbonate and alkanol.

Via a line 4 propylene carbonate is fed into the upper part of the reactive distillation zone 1. Via a line 5 a transesterifiation catalyst is also passed into the upper part of zone 1. Methanol, fed into a lower part of zone 1 via lines 6 and 7a, passes upward, and, promoted by the transesterification catalyst, reacts with the propylene carbonate to form propylene glycol product and dimethyl carbonate. The propylene glycol is recovered from the bottom of the distillation zone 1 via a line 8. The bottom product in line 8 also contains the catalyst. Therefore the product is separated into a catalyst-containing fraction and a product fraction in a separation unit 9. The separation may be accomplished by distillation. The catalyst is recycled to the zone 1 via line 5, and the propylene glycol is recovered, optionally after further purification (not shown) via a line 10.

It is suitable to use a stoichiometric excess of methanol. Therefore, a mixture of methanol and dimethyl carbonate is passed from the top of the zone 1 via a line 11, and is passed to the first extractive distillation zone 2. Via a line 12 propylene carbonate is passed into the extractive distillation zone 2. The extractant, i.e. propylene carbonate, is fed into the extractive zone at a higher level than the mixture of methanol and dimethyl carbonate. The extractive distillation results in the separation of a methanol-rich product, that is passed from the top of the zone 2 via line 7. The product is split into two portions. One portion is recycled to the reactive distillation zone 1 as recycle methanol via line 7a. It is advantageous to feed the recycle methanol at a higher level into the reactive zone 1 than the (make up) methanol that is supplied via line 6. The other portion is passed to a separation unit 17 via line 7b. In the separation unit the stream is separated into a gaseous flow, containing the compounds with a lower boiling point than methanol, e.g. gaseous contaminants such as carbon dioxide, and a liquid flow, mainly methanol. The gaseous flow is discharged from the process via line 18. The liquid methanol is recycled to the extractive distillation zone 2 via line 7c.

From the bottom of the extractive distillation a mixture of mainly dimethyl carbonate and propylene carbonate is obtained. This mixture is passed to the second extractive reaction zone 3 via line 13. In this distillation the dimethyl carbonate is recovered via line 14 at the top, whereas the propylene carbonate is recovered at the bottom. Via a line 15 the propylene carbonate is split into a stream that via line 4 is fed into the reactive distillation zone 1, and a second stream that via lines 16 and 12 is recycled to the extractive distillation zone 2.

Figure 2:
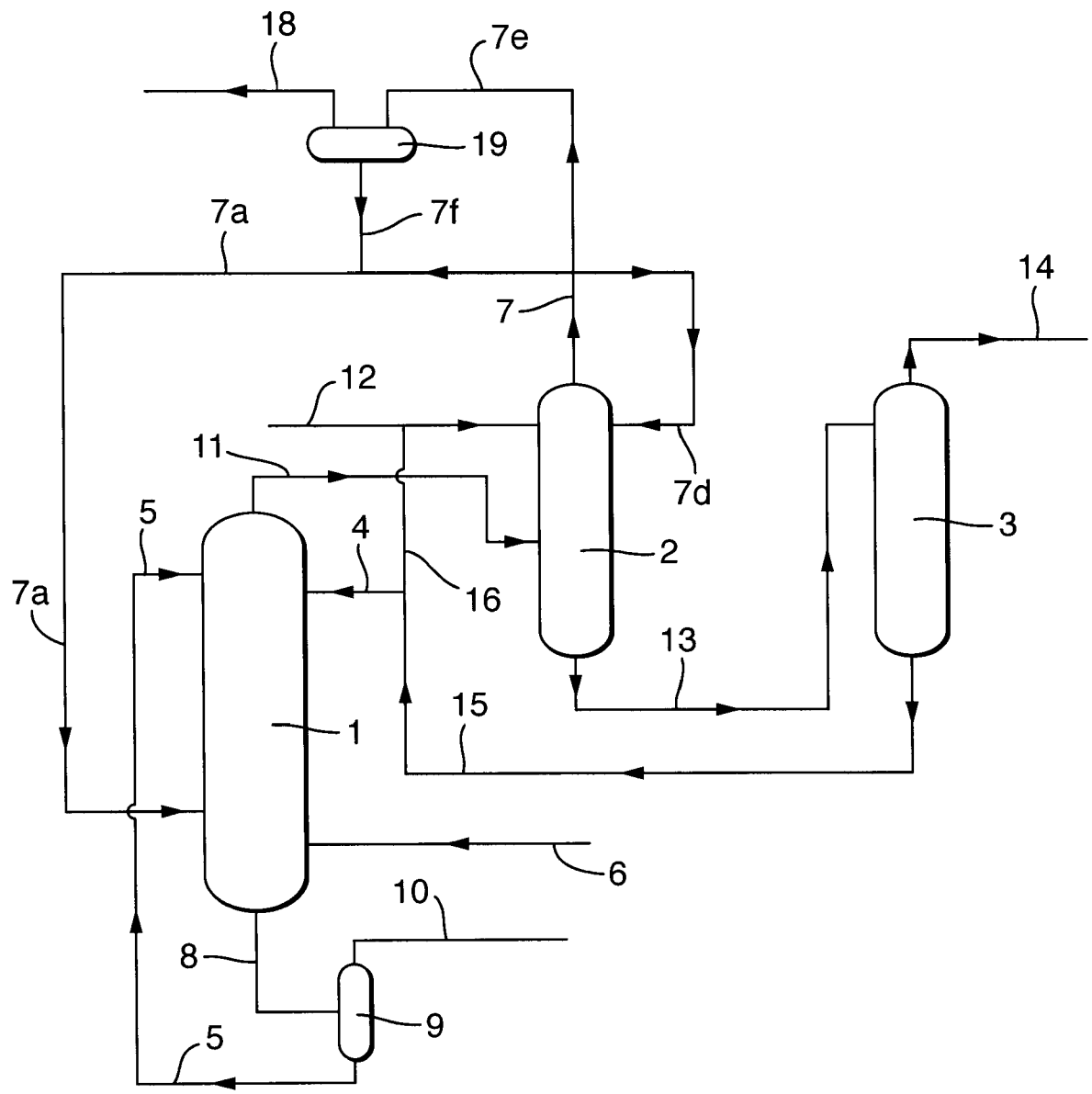
FIG. 2 is a schematic illustrating another embodiment of the invention in which the portion of the alkanol-rich stream that is freed from contaminants is recycled to the reactive distillation zone.

In FIG. 2 the same numbers apply to the same features as in FIG. 1. In the way as described for the process according to FIG. 1 a mixture of dimethyl carbonate and methanol leaves reactive distillation zone 1 via line 11, and is subjected to extractive distillation in extractive distillation zone 2. The methanol-rich product, separated from this mixture, is discharged from the top of the extractive distillation zone 2 via line 7. This product is split in at least two portions. One portion may be used as distillation reflux (indicated via line 7d). Another portion is passed straight back to the reactive distillation zone 2 via line 7a. A third portion is fed via line 7e to a cooling unit 19, where products with a boiling point below that of methanol, are separated. These lighter products are discharged via line 18. The cooled methanol is recycled via line 7f to the reactive distillation zone 1. The recycling may be accomplished by combining lines 7f and 7a (as shown), or by connecting line 7f separately to the reactive distillation zone.

EXAMPLE 1

To show the formation of by-products in a continuous process 120 g/h propylene carbonate and 1.5 g/h sodium methanolate in 15 g/h of a mixture of propylene glycol and methanol were continuously fed at the upper part of a reactive distillation column. In the lower part of the column 340 g/h methanol was fed. The reactive distillation column was operated at pressures varying from 135 to 105 kPa at temperatures ranging from 63 to 119° C. From the top of the column 365 g/h of a mixture of methanol and dimethyl carbonate was continuously withdrawn from the distillation column. The weight ratio of the withdrawn stream was about 70 wt % methanol and about 30% wt % dimethyl carbonate. The amount of by-products was as shown below.

TABLE

| By-product | Amount, ppm |
|---|---|
| Acetaldehyde | 20 |
| Propylene oxide | 450 |
| Propionaldehyde | 20 |
| Acetone | <20 |

The mixture was fed into an extractive distillation column to which 1400 g/h propylene carbonate was fed. A stream of 255 g/h methanol was obtained at the top of the extractive distillation column, which was operated at a temperature of about 180° C. and a pressure of 102 kPa. The methanol stream was over 99 wt % pure, but contained the following contaminants.

TABLE

| By-product | Amount, ppm |
|---|---|
| Acetaldehyde | 70 |
| Propylene oxide | 1000 |
| Propionaldehyde | 40 |
| Acetone | <20 |
| Dimethyl carbonate | 400 |

This example clearly shows that in a continuous process minor amounts of by-products are produced.

EXAMPLE 2

In a process as described in FIG. 1 7 t/h (tonnes per hour) propylene carbonate is fed into the upper part of a reactive distillation zone. Sodium methanolate in 0.5 t/h propylene glycol/methanol mixture as transesterification catalyst is also passed into the upper part of zone in an amount of 0.05 t/h. Twenty t/h methanol, fed into a lower part of the distillation zone, passes upward, and reacts with the propylene carbonate to form propylene glycol product and dimethyl carbonate. The propylene glycol is recovered in an amount of 5 t/h.

A mixture of methanol and dimethyl carbonate is withdrawn from the top of the reactive distillation zone and consists of 13 t/h methanol, 5.2 t/h dimethyl carbonate, 22 kg/h propylene oxide and about 55 kg/h of other volatile compounds. Via extractive distillation this mixture is separated. The separation yields a methanol-rich stream containing 13 t/h methanol, a trace of dimethyl carbonate, and all of the other mentioned by-products.

Half of this stream was condensed at 59.3° C. and 92 kPa yielding a vapour stream of 2 kg/h propylene oxide, about 25 kg/h of the other volatile compounds and 175 kg/h methanol. The vapour was bled. The liquid stream containing the rest of the methanol and the remainder of the by-products is recycled to the reactive distillation zone as part of the methanol feed.

It is evident that in this way the build up of by-products in the process is being controlled.

The invention claimed is:

1. A process for the preparation of an alkanediol and a dialkyl carbonate comprising:
    (a) contacting an alkylene carbonate with an alkanol feedstock under transesterification conditions in a reactive distillation zone to obtain a top stream comprising dialkyl carbonate and the alkanol and a bottom stream comprising an alkanediol;
    (b) separating the top stream comprising dialkyl carbonate and the alkanol into an alkanol-rich stream and a dialkyl carbonate-rich stream;
    (c) recovering the dialkyl carbonate from the dialkyl carbonate-rich stream; and
    (d) recycling at least part of the alkanol-rich stream to the reactive distillation zone as part of the alkanol feedstock,
    wherein the alkanol-rich stream is split in at least two portions, and at least one portion is condensed and freed from compounds with a lower boiling point than the alkanol.

2. A process according to claim 1, in which the separation of step (b) is carried out in the presence of the alkylene carbonate.

3. A process according to claim 1, in which the portion of the alkanol-rich stream that is freed from compounds with a lower boiling point than the alkanol is recycled to the reactive distillation zone.

4. A process according to claim 1, in which the portion of the alkanol-rich stream that is freed from compounds with a lower boiling point than the alkanol is recycled to the separation of step (b).

5. A process according to claim 1, in which the weight ratio between the portion to be condensed and the other portion is from 0.1:1 to 1:1.

6. A process according to claim 1, in which the alkylene carbonate is propylene carbonate and the alkanol is methanol.

7. A process according to claim 1 in which the dialkyl carbonate in the dialkylcarbonate-rich stream is subjected to further purification.

\* \* \* \* \*